US012213718B2

(12) United States Patent
Trumer et al.

(10) Patent No.: US 12,213,718 B2
(45) Date of Patent: Feb. 4, 2025

(54) CRYOPROBE WITH STIFFENING ELEMENT

(71) Applicant: Biocompatibles UK Limited, Camberley (GB)

(72) Inventors: Dror Trumer, Yokneam (IL); Satish Ramadhyani, Minneapolis, MN (US); Modechay Bleiwies, Kiryat Haim (IL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 212 days.

(21) Appl. No.: 16/672,156

(22) Filed: Nov. 1, 2019

(65) Prior Publication Data

US 2020/0138499 A1    May 7, 2020

Related U.S. Application Data

(60) Provisional application No. 62/823,366, filed on Mar. 25, 2019, provisional application No. 62/754,352, filed on Nov. 1, 2018.

(51) Int. Cl.
*A61B 18/02* (2006.01)
*A61B 17/00* (2006.01)
*A61B 18/00* (2006.01)

(52) U.S. Cl.
CPC ...... *A61B 18/02* (2013.01); *A61B 2017/0042* (2013.01); *A61B 2018/00017* (2013.01);
(Continued)

(58) Field of Classification Search
CPC .......... A61B 18/02; A61B 2018/00017; A61B 2018/00023; A61B 2018/00041; A61B 2018/0262; A61B 2018/0293
See application file for complete search history.

(56) References Cited

U.S. PATENT DOCUMENTS 5,108,390 A * 4/1992 Potocky ................. A61B 18/02
606/21
5,254,116 A   10/1993 Baust et al.
(Continued)

FOREIGN PATENT DOCUMENTS

EP    3873365 A1    9/2021
GB    2289413       11/1995
(Continued)

OTHER PUBLICATIONS

International Search Report and Written Opinion received for PCT Patent Application No. PCT/US2019/059503, dated Apr. 20, 2020, 13 pages.
(Continued)

*Primary Examiner* — Daniel W Fowler
(74) *Attorney, Agent, or Firm* — Pauly, DeVries Smith & Deffner LLC

(57) ABSTRACT

Aspects of the present invention provide miniaturized cryoprobes having shaft diameters up to 2 mm and including a stiffening element that may act as a grip for manipulation of the cryoprobe. Various aspects of the present disclosure are generally directed towards apparatuses, systems, and methods that may include a cryoprobe: In certain instances, the cryoprobe may include an elongate shaft and an operating head having an expansion chamber. The elongate shaft may include a first passageway configured to provide high pressure gas to the expansion chamber, a second passageway for evacuating gas from the expansion chamber, and a vacuum chamber coaxially arranged around the first passageway and the second passageway.

19 Claims, 4 Drawing Sheets

(52) U.S. Cl.
CPC .............. *A61B 2018/00023* (2013.01); *A61B 2018/00041* (2013.01); *A61B 2018/0262* (2013.01); *A61B 2018/0293* (2013.01)

(56) References Cited

U.S. PATENT DOCUMENTS

| | | | |
|---|---|---|---|
| 5,478,330 | A | 12/1995 | Imran et al. |
| 5,645,549 | A * | 7/1997 | Boyd .................. A61B 18/1482 606/45 |
| 5,716,353 | A * | 2/1998 | Matsuura .............. A61B 18/02 606/22 |
| 5,833,604 | A | 11/1998 | Houser et al. |
| 5,885,276 | A | 3/1999 | Ammar et al. |
| 5,992,158 | A * | 11/1999 | Goddard ................ A61B 18/02 606/24 |
| 6,039,730 | A * | 3/2000 | Rabin .................... A61B 18/02 606/21 |
| 6,251,128 | B1 * | 6/2001 | Knopp ............... A61B 18/1492 607/101 |
| 6,379,348 | B1 * | 4/2002 | Onik ....................... A61B 18/02 606/49 |
| 2002/0143323 | A1 * | 10/2002 | Johnston ................ A61B 34/35 606/22 |
| 2003/0055415 | A1 | 3/2003 | Yu et al. |
| 2003/0060815 | A1 * | 3/2003 | Lalonde ................. A61B 18/02 606/23 |
| 2004/0210212 | A1 | 10/2004 | Maurice |
| 2006/0030849 | A1 * | 2/2006 | Mirizzi .................... A61F 7/123 606/50 |
| 2006/0079867 | A1 | 4/2006 | Berzak et al. |
| 2006/0264920 | A1 * | 11/2006 | Duong .................. A61B 18/02 606/21 |
| 2007/0112343 | A1 * | 5/2007 | Mische ................. A61B 18/20 606/41 |
| 2009/0036823 | A1 * | 2/2009 | LePivert ............... A61B 18/02 604/21 |
| 2009/0192505 | A1 * | 7/2009 | Askew .............. A61M 16/0463 424/9.4 |
| 2011/0028960 | A1 | 2/2011 | Tin |
| 2011/0264084 | A1 * | 10/2011 | Reid ..................... A61B 18/02 606/23 |
| 2014/0350536 | A1 | 11/2014 | Allison |
| 2014/0371742 | A1 * | 12/2014 | Fruehauf ............. A61B 18/1492 606/41 |
| 2015/0230850 | A1 * | 8/2015 | McKay .............. A61B 18/0218 606/23 |
| 2020/0138499 | A1 | 5/2020 | Trumer et al. |
| 2020/0305948 | A1 | 10/2020 | Trumer et al. |

FOREIGN PATENT DOCUMENTS

| | | |
|---|---|---|
| GB | 2289413 A | 11/1995 |
| JP | 44-015357 B | 7/1969 |
| JP | 51-111789 U | 9/1976 |
| JP | 07-501240 A | 2/1995 |
| JP | 11-276495 A | 10/1999 |
| JP | 2005-514167 A | 5/2005 |
| JP | 2005-534405 A | 11/2005 |
| JP | 2007501240 | 1/2007 |
| JP | 2009-112563 A | 5/2009 |
| JP | 2013-500791 A | 1/2013 |
| JP | 7476294 | 4/2024 |
| WO | 93/04647 A1 | 3/1993 |
| WO | 93004647 | 3/1993 |
| WO | 03/59247 A2 | 7/2003 |
| WO | 2005/000106 A2 | 1/2005 |
| WO | 2005000106 | 1/2005 |
| WO | 2018/087563 A1 | 5/2018 |
| WO | 2020092981 A1 | 9/2021 |

OTHER PUBLICATIONS

International Search Report and Written Opinion received for PCT Patent Application No. PCT/US2020/024374, dated Jul. 13, 2020, 13 pages.

"Response to Office Action," for Canadian Patent Application No. 3,114,794 filed Dec. 21, 2023 (10 pages).

"First Examination Report," for Australian Patent Application No. 2022283628 mailed Mar. 21, 2024 (5 pages).

"Response to First Examination Report," for Australian Patent Application No. 2022283628 filed Jun. 25, 2024 (12 pages).

* cited by examiner

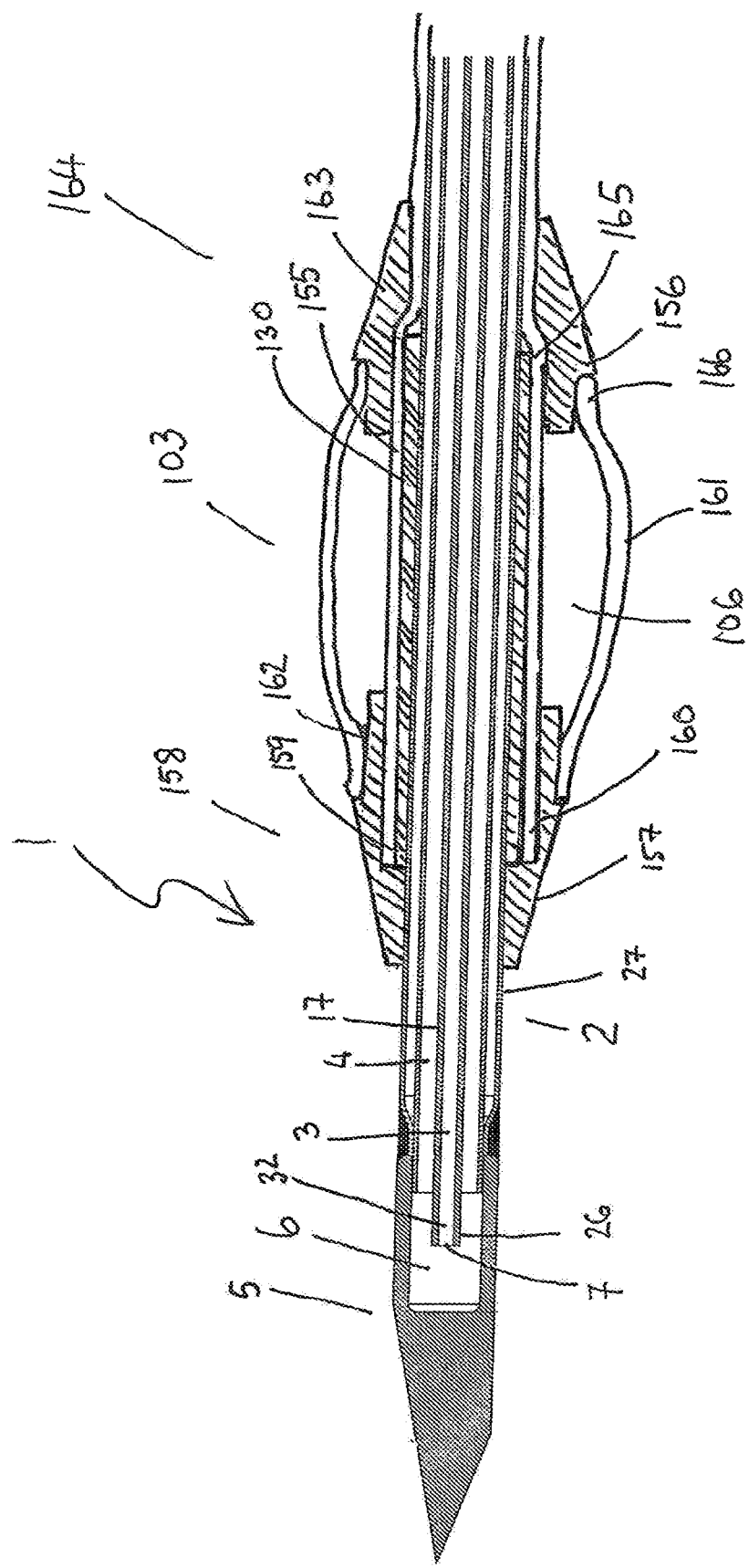

CRYOPROBE WITH STIFFENING ELEMENT

This application claims priority to Provisional Application No. 62/823,366, filed Mar. 25, 2019, Provisional Application 62/754,352, filed Nov. 1, 2018, all of which are herein incorporated by reference in its entirety.

BACKGROUND

This disclosure relates to a cryoprobe for use in cryoablation and a system for cryoablation.

During cryosurgery, a surgeon may deploy one or more cryoprobes to ablate a target area of a patient anatomy by freezing and thawing the tissue. In one example, a cryoprobe uses the Joule-Thomson effect to produce cooling or heating of the probe tip. In such cases, the expansion of a cryofluid in the cryoprobe from a higher pressure to a lower pressure leads to cooling of the device tip to temperatures at or below those necessary for cryoablating a tissue in the vicinity of the tip. Heat transfer between the expanded cryofluid and the outer walls of the cryoprobe leads to formation of an "ice ball," in the tissue around the tip and consequent cryoablation of the tissue.

Cryoprobes may be in the form of needles that are deployed transcutaneously. A common cryoablation technique uses multiple cryoneedles in combination, each of which may be individually controlled to cryoablate a pre-planned three-dimensional ablation volume. Using an array of such cryoprobes allows the shape of the ablation volume to be controlled and allows for accurate three-dimensional placement of the ice balls that are formed in a manner that conforms to the dimensions, form, and location of the tissue to be ablated. A disadvantage of this technique, however, is that because multiple cryoprobes are introduced they may become difficult to control and handle as the operating area becomes more crowded. Commercially available cryoprobes are provided with either straight or bent shafts in order to make placement easier.

Cryoneedle shafts often have a length of about 150 to 250 mm. As a consequence of the shaft length, the turning moment on the shaft in situ is relatively large, which can affect the ease of positioning and the lateral forces on the tip within the tissue. This is especially pronounced when ablating tissues within a few centimeters of the surface.

Further, currently available devices are configured to produce relatively large ice balls, and so are less useful where small ablations are required or more critical sculpting is needed, such as around delicate tissues.

SUMMARY

Accordingly, in a first aspect, the present disclosure provides a cryoprobe for use in cryoablation, comprising: an elongate shaft having a distal end and a proximal end; an operating head at the distal end of the elongate shaft, wherein the operating head comprises an expansion chamber; the elongate shaft comprising a first passageway for providing high pressure gas to the expansion chamber and wherein the first passageway terminates in a Joule-Thomson orifice at its distal end, a second passageway for evacuating gas from the expansion chamber, wherein the second passageway is coaxially arranged around the first passageway, and a vacuum chamber coaxially arranged around the first passageway and the second passageway; the cryoprobe additionally comprising an elongate stiffening element located towards the distal end of the elongate shaft and in fixed engagement therewith, the stiffening element configured to reduce flexing of the elongate shaft over the length of the stiffening element during use.

The cryoprobe is, for example, a cryoneedle for percutaneous use.

The elongate shaft has a distal end and a proximal end and comprises a first passageway, a second passageway, and a vacuum chamber. The diameter of the shaft is defined by the outer diameter of the vacuum chamber.

An operating head is provided at the distal end of the elongate shaft.

The cross section of the elongate shaft is from 0.9 to 2.0 mm in diameter at its widest point. Preferably the elongate shaft is from 0.9 to 1.4 mm in diameter, particularly 1.0 to 1.3 mm in diameter, most preferably the elongate shaft is 1.2 mm+/−0.1 mm in diameter.

The shaft and operating head combined extend distally beyond the stiffening element (measured from the tip of the operating head to the distal most extent of the stiffening element, at a position adjacent the shaft), up to 100 mm, preferably from 8 to 60 mm, more preferably 20 to 40 mm in length, and most preferably 30 mm+/−5 mm in length.

The shaft extends proximally beyond the stiffening member as a "tail" and terminates proximally at a union configured to connect at least the first passageway to a source of cryofluid, such as a cryogas. The union may also be configured to receive the outlet tube and to provide an opening to allow exhaust of the returning cryogas to the atmosphere. The union may also be configured to connect the first passageway to a source of heating gas, such as helium.

Proximal of the stiffening element, the shaft may additionally comprise a protective cover. The cover is configured to allows the shaft to flex, but reduces or prevents kinking of the shaft. The protective cover may extend distally beyond the proximal most portion of the stiffening element, and may cover at least a portion of the tail region extending proximally from the stiffening element.

The first passageway is typically defined by and is co-extensive with an inlet tube having an outer circumferential wall. The first passageway provides high pressure gas to the expansion chamber from a source of cryogas (or heating gas). Preferably, the first passageway extends into the expansion chamber, terminating within the chamber at or near its distal most end. The inlet tube extends proximally to the proximal end of the tail region. The inlet tube typically terminates in a connector as described above.

The inlet tube is sized to fit within the second passageway and has sufficient cross-sectional area of the second passageway to provide for efficient exhaustion of the gas. Thus, the diameter of the inlet tube may be determined by the required flow characteristics of the device. Dependent on the desired external diameter of the device the inlet tube may be for example 0.25 to 0.5 mm in outside diameter, preferably 0.3 to 0.4 mm. The first passageway may be 0.15 to 0.25 mm in diameter, preferably 0.15 to 0.2 mm.

The inlet tube is typically metallic, and for example, may be made of stainless steel.

High pressure gases that are suitable for use as a cryogas or cryofluid include $CO_2$, argon, nitrogen air, krypton, $CF_4$, xenon or $N_2O$; preferably, the cryogas is argon. As used herein, the term "high-pressure" as applied to a gas refers to gas pressures appropriate for Joule-Thomson cooling of cryoprobes. In the case of argon gas, for example, "high-pressure" argon is typically between 3000 psi and 4500 psi, although somewhat higher and lower pressures may sometimes be used.

Expansion of high pressure gasses through a Joule-Thomson orifice may also be used to provide heating. Certain gases ("heating gases"), when passed through a Joule-Thomson orifice, become warmer rather than cooler (e.g., when passed through at room temperature or warmer). Helium is an example of a gas having this property. Thus, passing helium through a Joule-Thomson orifice has the effect of warming the probe tip and accelerating tissue thawing.

The first passageway terminates in a Joule-Thomson orifice at its distal end, which can be located within the expansion chamber in the operating head. When high pressure gas is fed through the first passageway and exits through the Joule-Thomson orifice it expands causing it to cool. The cooled expanded gas, and any liquefied gas formed, cool the outer surface of the operating head and thereby freeze adjacent body tissue to produce the desired cryoablative effect.

The first passageway is also able to deliver heating gases, such as helium. Heating gases have an inversion temperature lower than temperature obtained by liquefaction of cooling gas, or a negative Joule-Thomson co-efficient even at temperatures as low as those obtained by liquefaction of the cooling gas. The first passageway is therefore configured so as to be coupleable to a first gas source, supplying a high pressure cryogas, and also to be coupleable to a second gas source supplying high pressure heating gas. Coupling to the first and second gas may be through the same proximal union, since switching between the gas sources is typically controlled by a control unit.

The cryoprobe according to the present disclosure is therefore able to quickly switch from cooling to heating, to improve the speed of the procedure, and to more easily prevent sticking of the operating head to the tissue. The cryoprobe is also able to induce fast cyclical temperature changes in the cryoprobe such that the temperature of the probe alternates rapidly between a temperature of approximately 0° C. and a temperature below −40° C.

The second passageway evacuates gas from the expansion chamber towards the exhaust. The second passageway is typically defined by and co-extensive with an outlet tube that evacuates the gas and has an inner circumferential wall and an outer circumferential wall. The second passageway is coaxially arranged around the first passageway such that the first and second passageways may share a common circumferential wall, wherein the inner circumferential wall is the same wall as the outer circumferential wall of the inlet tube. Preferably, the proximal end of the second passageway is open to the atmosphere.

The second passageway is of sufficient cross-sectional area to allow efficient return flow of the exhausted gas, thus the diameter of the outlet tube may be determined by the required flow characteristics of the device. This provides a simple counter flow recuperative heat exchanger. Dependent on the desired external diameter of the device the second passageway may be for example 0.6 to 1.2 mm in diameter, preferably 0.7 to 0.8 mm.

The outlet tube is typically metallic, and for example, may be made of stainless steel.

The coaxial arrangement of the first and second passageways acts as a simple heat exchanger. The expanded gas at the proximal end of the second passageway is colder than the high pressure gas in the first passageway at that point, and thus cools the high pressure cryogas being fed towards the expansion chamber. This arrangement also provides a positive feedback mechanism whereby during continued use the cryogas being fed through the first passageway gets colder and colder as does the gas being evacuated via the second passageway.

As the cooled, expanded gas returns via the second passageway, which is formed circumferentially about the inlet tube, it cools the incoming gas in the inlet tube in a simple counter current heat exchange mechanism.

Thus, the device may comprise a single heat exchange arrangement involving the exchange of heat energy between the inlet tube and outlet tube arranged linearly and concentrically within the shaft. This arrangement allows the shaft itself to be of a uniform diameter from the proximal end to the distal end.

This serves as the only heat exchange mechanism necessary for the formation of an ice ball about the tip of the device. Due to the size of the probe, and the small size of ice ball produced, no further heat exchanger is required. For example, no helical coil heat exchangers, typically found in cryoablation devices, are necessary. This saves weight in the grip of the device, where heat exchange arrangements are typically situated.

The second passageway extends from proximal end to distal end of the outlet tube with no additional heat exchange features. Likewise, the first passageway extends from the proximal end to the distal end of the inlet tube with no additional heat exchange features. Thus, the inlet tube extends proximally from the union to the distal most end situated in the expansion chamber, and the outlet tube extends distally from the vent to atmosphere (typically from the union) to the operating head with little or no interruption to the flow in either tube.

Due to the lack of other heat exchange arrangements, resistance to flow of cryogas through the first passageway is uniform throughout the shaft, and the resistance to flow of the returning cryogas in the second passageway is uniform throughout the shaft. Neither flow in the inlet tube nor the flow in the outlet tube is influenced (e.g., obstructed, diverted, split, or slowed) by heat exchange arrangements with the other tube, such as helical heat exchangers.

The vacuum chamber has an inner circumferential wall and an outer circumferential wall, whereby the outer circumferential wall defines the outer circumference of the elongate shaft of the probe. In some examples, the vacuum chamber is coaxially arranged around the first and second passageways such that the vacuum chamber shares a circumferential wall with the second passageway, for example, wherein the inner circumferential wall of the vacuum chamber is the same wall as the outer circumferential wall of the second passageway. The vacuum chamber extends distally as far as the operating head but does not extend over the operating head. This limits the extent of the ice ball to the distal end of the device, including the operating head, and protects tissue surrounding the more proximal portions of the shaft from low temperatures. It also allows the operator to handle the cryoprobe safely. The arrangement in which the vacuum chamber inner wall also forms the outer wall of the second passageway allows the device to be constructed so as to minimize the shaft diameter and enables a cryoprobe of very thin dimensions.

Preferably, the outlet tube extends distally beyond the distal most extent of the vacuum chamber. This enables the distal most end of the outlet tube to extend into the proximal chamber of the operating head and provides a firm mount for attaching the operating head. Preferably, the inlet tube extends beyond the distal most end of the outlet tube into the expansion chamber formed beyond the distal most end of the outlet tube.

Preferably, the outer wall of the vacuum chamber is tapered at its distal end such that the tapered end of the vacuum chamber forms a union with the outer wall of the outlet tube. This provides a circumferential indentation between the vacuum chamber outer wall and the operating head. Preferably, the outer wall of the vacuum chamber is a push fit over the outlet tube. This allows for easy assembly of the device and helps to minimize the total outer diameter of the device. Preferably, the operating head is welded or soldered to the vacuum tube and/or the outlet tube. This arrangement allows the outer wall of the vacuum tube to be easily attached to the outer wall of the outlet tube. In one approach, the vacuum sleeve outer wall is welded or brazed to the outer wall of the outlet tube in a vacuum furnace before being attached to the operating head.

Preferably, the surface of the operating head and the outer tube of the vacuum sleeve provide a continuous surface of uniform diameter. The presence of the circumferential indentation provides for a strong weld or solder joint between the operating head and the outlet tube and/or vacuum tube and allows the device to have a continuous surface of uniform diameter. The joint is preferably laser welded.

The operating head is preferably formed from a single solid piece of material (e.g., as a monolithic unit). The operating head comprises a chamber open at the proximal end and having a chamber wall surrounding the chamber and extending from the proximal end of the operating head to the distal end of the chamber. The proximal chamber of the head is typically from 1 to 3 mm deep preferably from 1 to 2 mm deep. The diameter of the head is approximately the same as that of the shaft, to provide a smooth uniform outer surface. Distal of the chamber, the operating head is solid. The operating head may have a blunt distal end, but preferably the operating head has a sharp distal end configured to penetrate tissue, preferably in the form of a three-sided, trocar-type tip. The operating head is typically between 2 and 10 mm long, measured from the tip to the proximal most point on the chamber wall. The proximal portion of the chamber wall preferably forms a union with the distal end of the outlet tube. Preferably, the inner surface of the proximal portion of the chamber wall forms a union with the outer surface of the distal end of the outlet tube, preferably as a push fit. The expansion chamber of the device is formed between the distal end of the chamber and the distal end of the outlet tube. The chamber is bounded by the chamber walls.

Preferably, the operating head is from 2 to 7 mm in length measured from the point at which the operating head meets the distal most end of the vacuum chamber to the distal end of the operating head (this is shown in FIG. 1). Preferably, the operating head is 2.5 to 6 mm in length, and more preferably, the operating head is 4 mm+/−1.5 mm in length.

Preferably, the operating head is formed from heat conducting material such as metal, e.g., stainless steel, for effectively freezing body tissue coming into contact with the operating head. In one embodiment, the operating head has an outer sheath layer that is also preferably formed from heat conducting material.

The probe comprises an elongate stiffening element, which is located towards the distal end of the elongate shaft. This element serves as a support for the shaft during manipulation, and is configured to reduce and preferably to prevent flexing of the elongate shaft over the length of the stiffening element during use. The shaft is otherwise quite malleable due to its narrow nature and the thinness of the walls of the tubular elements making up the shaft (inlet tube, outlet tube and vacuum chamber outer wall). The stiffening element is elongated along the axis of the shaft in order to provide sufficient support for the shaft. The stiffening element may act as a grip for manipulating the shaft. It is typically in fixed engagement with the shaft to prevent the shaft moving relative to the element when the tip is pushed into tissue. In one arrangement, the stiffening element is a disposed about the shaft, for example, it may be coaxially and/or circumferentially arranged about the shaft. It may for example be a reinforcing tube arranged coaxially about the shaft.

The stiffening element may be in the form of a grip or handle, or a grip may be provided in addition to the stiffening element. The grip serves also to improve grip on the shaft. Typically, the grip may be coaxial with the elongate shaft. Preferably, it is of a larger diameter than the vacuum sleeve and is typically of a size and shape suitable for gripping comfortably with the hand. The grip not only serves to provide a portion suitable to manipulate the probe, but also strengthens the shaft at this point to prevent it bending while it is being manipulated. The grip may be provided with an insulating layer which may be either an insulating material, a further vacuum chamber, or a combination or both. The grip may be provided with a polymer sheath to aid in gripping the device during manipulation. The sheath may also be used to carry identifying markings of the device, such as probe size and type.

The cryoablation devices of the disclosure may be provided with either straight shafts or angled shafts in which the shaft is bent to provide less crowding at the insertion site, typically an approximately right angled bend is used.

Typically, the inlet tube and outlet tube are continuous through the grip part of the device. Preferably, they extend beyond the proximal extent of the grip to provide a high pressure gas inlet and low pressure gas return line, respectively. The high pressure gas inlet preferably terminates proximally in a connector suitable for connection to source of cryogas. The return line preferably terminates at an opening to release the returned gas to atmosphere.

The outer wall of the vacuum chamber may extend through the grip portion. It may further extend proximally to insulate at least a portion of the gas return line, proximally of the grip. The high pressure gas inlet and low pressure gas return line (and the vacuum chamber if present) may be provided with an outer protective tube to prevent damage to the lines.

In a further aspect of the disclosure, there is provided a system for cryoablation comprising one or more cryoprobes as described herein. Typically, such systems include one or more cryoprobes, such as cryoneedles, suitable for transcutaneous use, one or more cryofluid sources, and a control system. Cryosurgical systems can be used for cryoablating target tissues (e.g., a tumor). By selecting the appropriate cryofluid and pressure, they can be used to cool tissue to a greater or lesser extent.

The cryofluid sources can supply gases such as argon, nitrogen, air, krypton, $CO_2$, $CF_4$, xenon, and various other gases that are capable of reaching cryogenic temperatures (e.g., temperatures below 190 Kelvin) when expanded from pressures greater than about 1000 psi. As used herein, "cryofluid" can refer to any fluid that reaches low temperatures (e.g., below 190 Kelvin) when expanded from pressures greater than about 1000 psi (e.g., typically around 3500 psi). The source may comprise one or more valves and/or regulators to control the flow of cryo and heating fluids.

The control system is configured to control the delivery of cryofluid to the cryoprobe(s), and may comprise, for example, one or more sensors, flow meters, timers, analogue/digital converters, wired or wireless communication modules, valve controllers, etc. Additionally, the control system can also regulate the flow rate, temperature, and pressure of cryofluid supplied to the cryoprobe.

In a further embodiment, there is provided a method of ablating a patient tissue comprising: placing the tip of a cryoprobe as described herein within, at, or close to the tissue to be ablated; delivering a cryogas to the Joule-Thomson orifice, via the first passageway, at a pressure sufficient to cause cooling of the probe tip to a cryogenic temperature, and thereby to freeze patient tissue in contact with the probe tip; and subsequently thawing the tissue.

The tissue is thawed at least sufficiently such that the probe may be removed if needed, however, typically several cycles of freezing and thawing are carried out, e.g., two, three, or more cycles. Rather than allowing the tissue to thaw naturally, in an alternative approach, a warming gas is delivered to the Joule-Thomson orifice at a pressure sufficient to cause warming of the probe tip and thus thawing of the tissue.

Typically the freezing operation forms an "ice ball" of frozen tissue around the probe tip.

In some approaches, a cooling gas such as nitrous oxide may be used in place of the cryogas. The expansion of such gases on exit from the Joule-Thomson orifice does not lead to cooling to cryogenic temperatures, but does lead to a temperature low enough to cause disruption or damage to the tissue but not to kill it. This approach is particularly useful when the probe is used for cryoneurolysis of nerve tissue, which is able to regrow following exposure to such temperatures, but not following exposure to cryogenic temperatures.

One or more cryoprobes are placed at or close to a tissue to be treated by ablation. A high pressure gas, such as argon, is delivered to the cryoprobe to cause the formation of an ice ball at the tip of the probe that encompasses the tissue to be treated. Ice ball formation may be followed using an imaging procedure, such as ultrasound or MM, and the cooling stopped when the ice ball reaches the desired size. The ice ball may then be thawed naturally using body temperature, or thawing may be accelerated by delivering a heating gas such as helium to warm the tip of the probe. Helium thawing is preferred because it is faster.

Typically, one or more iceball formation and thawing cycles are employed to ablate the target tissue. Typically, one, two, or three cycles are used.

Cryoablation of tumors is known to produce an abs copal effect in lesions remote from those treated. Where one tumor is ablated using cryoablation, other tumors remote from the first tumor have been observed to shrink. This effect is believed to be mediated by the release of tumor antigens, which prime the immune system to recognize the remote tumor (see for example Mehta et al 2016, Gastroenterology Research and Practice Volume 2016, Article ID 9251375).

As a result of these observations, it has been proposed to treat tumors using a combination of cryoablation and various immune modulators (see for example Abdo et al 2018, Frontiers in Oncology. Volume 8 article 85).

In one approach to treatment, cryoablation of the tumor may be used in combination with an immunomodulatory drug administered before, during, or after cryoablation treatment. Such drugs include checkpoint inhibitors such as anti CTLA-4 anti-PD-1 and anti PDL-1 antibodies, for example, including ipilimumab, nivolumab, pembrolizumab, atezolizumab, avelumab, and durvalumab.

The present probes are also particularly suitable for use in the treatment of pain by partial (axonotmesis) or complete ablation of the nerve (neurotmesis).

By utilizing cryoprobes where the elongate shaft has a reduced dimension (e.g., cryoprobes of the present disclosure that have a reduced shaft length and diameter) it is possible to increase the number of cryoprobes present at the ablation site, because crowding is reduced. This further enhances the ability to accurately sculpt a three-dimensional ablation target site given that an increased number of cryoprobes can fit into a given area. Furthermore, by using a combination of straight and bent cryoprobes, an even greater number of cryoprobes may be deployed in a given area at the ablation site, further reducing crowding when multiple cryoprobes are deployed.

The small diameter and short length also makes the probes useful in accessing small volumes of tissue for which normal probes would be difficult or impossible to use accurately. They are particularly useful for the treatment of conditions in infants.

A further particular condition that is treatable using the present probes is Morton's neuroma, a benign neuroma of an intermetatarsal plantar nerve, which is inaccessible to standard probes due to their size.

BRIEF DESCRIPTION OF THE DRAWINGS

Aspects of the invention will now be described further by way of the following non limiting examples with reference to the figures. These are provided for the purpose of illustration only and other examples falling within the scope of the claims will be readily apparent to those skilled in the art in the light of these. All literature references cited herein are incorporated by reference.

FIG. 1A illustrates a joint arrangement between the operating head and the shaft in higher magnification.

FIG. 4 is a simplified illustration of features of the cryoprobe with a further example of a stiffening element. The device is shown in cross section.

EXAMPLE

Cryoneedles were constructed according to the description above having an inlet tube of 0.18 mm inner diameter and 0.33 mm outer diameter. An outer tube of 0.72 mm inner diameter and an overall diameter of 1.2 mm including the vacuum sleeve. The operating head was approximately 5 mm in length. The whole device from tip to proximal end of the tail was 3 m in length and the shaft and operating head combined extended from the stiffening element by 30 mm.

Using argon delivered at 3500 psi these needles produced ice balls of 10 mm in diameter in 2 minutes, 14 mm in diameter at 3.5 minutes, and 15 mm in diameter at 5 minutes.

DETAILED DESCRIPTION

Figures

Figure 1:
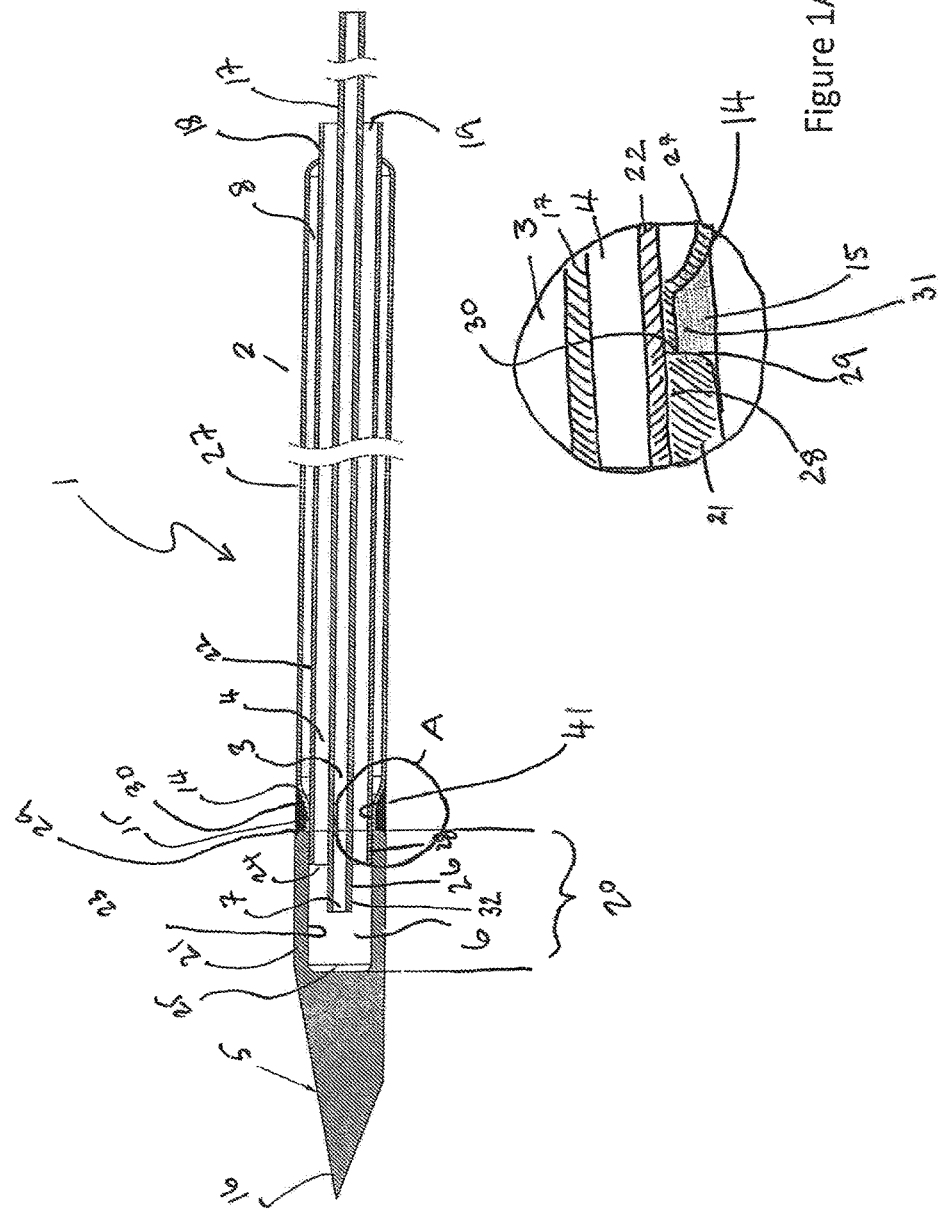
FIG. 1 is a simplified illustration of features of the cryoprobe shaft, shown in cross section.

FIG. 1 represents a cross section of a simplified view through a cryoprobe (1). The cryoprobe (1) has an elongate shaft (2) including an operating head (5) having tip (16). The elongate shaft (2) encloses a first passageway (3) which is co-extensive with an inlet tube (17). A second passageway (4) is co-extensive with an outlet tube (18). The first passageway (3) and second passageway (4) are concentric, wherein the second passageway (4) surrounds the first passageway (3). The second passageway (4) may be open to the atmosphere proximally via an outlet (19).

The operating head (5) comprises an operating head proximal chamber (20) surrounded by chamber walls (21) and distally by a distal end wall (25). The outlet tube (18) may project into the proximal chamber (20) of the operating head (5). An expansion chamber (6) may be formed between the distal end (24) of the outlet tube (18) and the distal end wall (25) of the operating head proximal chamber (20). The expansion chamber may be bounded by the inner walls (23) of the operating head proximal chamber (20). The distal most end (26) of the inlet tube (17) typically projects into the expansion chamber (6) and may terminate in a Joule-Thomson orifice (7) which is formed at the distal most end of the first passageway (3).

The inlet tube (17) is configured to deliver a cryogas under pressure from a cryofluid source (not shown in this figure). The cryogas expands on exiting the Joule-Thomson orifice (7) and evacuates via the outlet tube (18) to atmosphere at the opening (19).

The elongate shaft (2) further comprises a vacuum chamber (8) bounded externally by an outer circumferential vacuum chamber wall (27) and internally by the wall (22) of the outlet tube (18). The vacuum chamber is configured to thermally insulate the shaft proximal of the operating head and so prevent tissue damage proximal to the intended ice ball. Distally, the vacuum chamber wall (27) is tapered (14) and is a push fit over the outlet tube (18) at this point to provide a union between the two tubes (41). The vacuum chamber wall (27) may be welded or brazed to the wall of the outlet tube (18) in a vacuum furnace before being attached to the operating head. The distal most end (24) of the outlet tube (18) may project beyond the tapered end of the wall of the vacuum chamber (14) so as to be insertable into the proximal portion (28) of the operating head proximal chamber (20). The proximal end (29) of the wall (21) of the operating head proximal chamber (20) may be abutted against the distal end (30) of the vacuum chamber outer wall (27) to provide a circumferential indentation (31) between the vacuum chamber outer wall (27) and the proximal end (29) of the operating head distal chamber wall (21). The operating head (5), the vacuum chamber outer wall (27), and the outlet tube (18) can be welded or soldered together at this point (15) to seal the vacuum tube and hold the head in place.

FIG. 1A illustrates a close-up view of a joint between the operating head and the elongate shaft. Numbering is as for FIG. 1.

Figure 2:
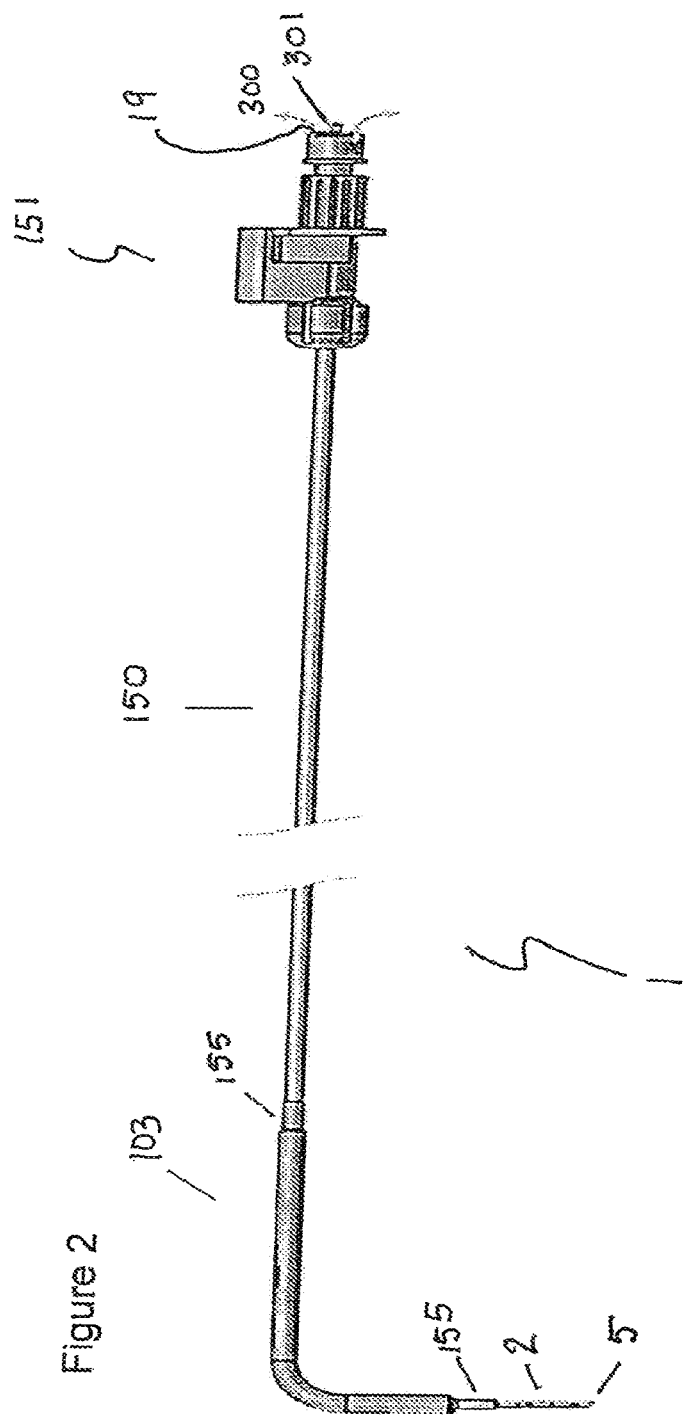
FIG. 2 is a pictorial view of a bent shaft arrangement of the cryoprobe.

FIG. 2 shows a cryoprobe (1) having a shaft (2) and a distal operating head (5). The shaft is in a bent configuration, which is useful to prevent overcrowding at the insertion site when more than one device is used. The shaft has a grip region 103 of larger outer diameter than the shaft, which is covered in a heat shrink cover (155). The shaft (2) extends proximally of the grip (103) as a tail region (150). In this region, the shaft is covered by a cover extending from the grip (103) to the proximal connector (151), which is configured for connection of the first passageway to a cryofluid source (not shown). The connector also comprises the distal outlet of the second passageway via outlet (19) for venting the low-pressure gas to the atmosphere (300). The connector further comprises an inlet (301) for coupling to a source of high pressure gas.

Figure 3:
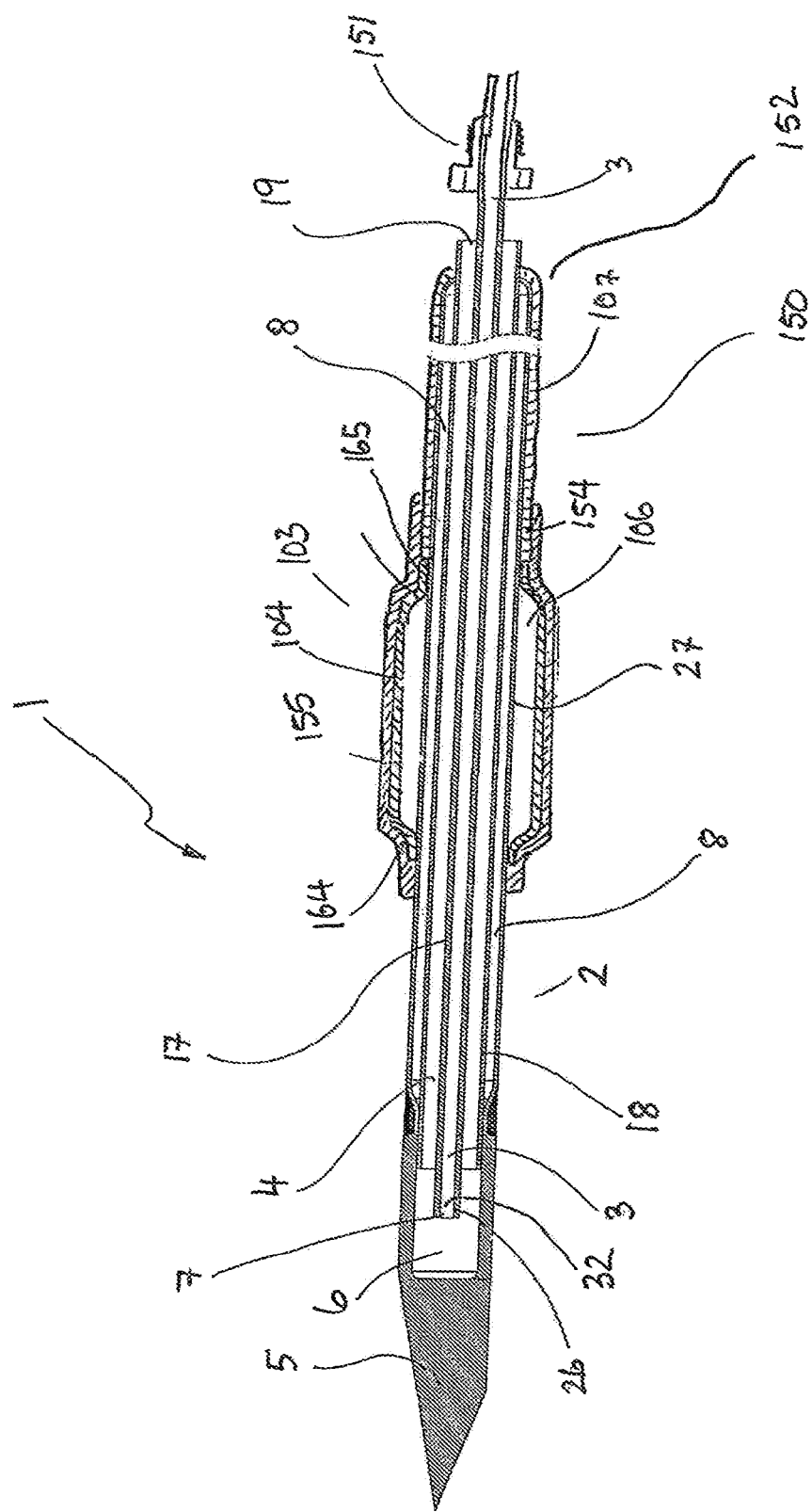
FIG. 3 is a simplified illustration of features of the cryoprobe with an example of a stiffening element. The device is shown in cross section.

FIG. 3 shows a section through a cryoprobe to illustrate features thereof. The cryoprobe (1) has a grip (103) that aids manipulation of the probe and acts to prevents flexing of the shaft during insertion into tissue and prevent kinking of the shaft. The cryoprobe has an elongate shaft (2) passing through and extending distally from the grip portion (103). An operating head (5) is provided distally of the elongate shaft (2). The shaft extends proximally of the grip (103) in the form of a tail portion (150), which terminates in a fitting (151) configured to connect the first passageway (3) to a cryofluid source (not shown).

The elongate shaft (2) encloses a first passageway (3) that is co-extensive with an inlet tube (17). A second passageway (4) is co-extensive with an outlet tube (18). The second passageway (4) may be open to the atmosphere proximally, e.g., via an outlet (19). The distal most end (26) of the inlet tube (17) typically projects into an expansion chamber (6) and may terminate in a Joule-Thomson orifice (7) that is formed at the distal most end (32) of the first passageway (3).

The inlet tube (17) is configured to deliver a cryogas under pressure from a cryofluid source (not shown in this figure). The cryogas expands on exiting the Joule-Thomson orifice (7) and evacuates via the outlet tube (18) to atmosphere at the opening (19).

A vacuum chamber (8) is formed over the outlet tube (18) and is bounded externally by an outer circumferential vacuum chamber wall (27). The vacuum chamber is configured to thermally insulate the shaft proximal to the operating head and so prevent tissue damage proximal to the intended ice ball.

The shaft (2) extends through the grip portion (103) and maybe continuous with the tail portion (150) as shown, or may form a union with a demountable tail portion (not shown).

The grip portion (103) has a diameter greater than the vacuum chamber wall (27) and provides a stiffened region of the shaft which prevents the shaft from flexing during manipulation and so prevents the shaft from kinking. In one arrangement, the grip portion comprises a sleeve (104) having a diameter greater than the vacuum chamber wall (27). The sleeve (104) may be of metal or polymer. In one approach, the sleeve may have tapered regions (164, 165) that provide a step down in sleeve diameter and provide a push fit over the vacuum chamber wall (27). The grip (103) may comprise a space (106) between the sleeve (104) and the vacuum chamber wall (27). The tapered regions of the sleeve (164, 165) are particularly useful in this case, particularly where the sleeve is metal as they allow a thin metallic sleeve to provide a wide grip portion with minimal weight, and provide stiffening to the sleeve. Where the space (106) is present it may be evacuated to provide additional insulation. The region between the vacuum chamber wall and the sleeve may also be filled with an insulating material.

The tail portion (150) may be provided with a covering (107), typically extending at least from the grip (103) to the proximal portion (152) of the tail (150). The covering (107) provides protection to the tail (150) and reduces kinking within the tail. The cover (107) may be loosely provided over the vacuum sleeve wall (27) within the tail region (150) or may be addressed to the vacuum sleeve wall (27). A coating (155) may be provided over the sleeve to seal the sleeve to the vacuum chamber wall (27). It may also extend to hold the distal end (154) of the cover (107) in place. This coating (155) may comprise a heat shrink sleeve, for example.

FIG. 4 illustrates a further embodiment of the grip portion. The cryoprobe (1) has a grip (103) for manipulation of the probe, and to prevent flexing of the probe during use and thereby prevent kinking of the shaft (2). The cryoprobe has an elongate shaft (2) passing through and extending distally from the grip portion (103). An operating head (5) is provided distally of the elongate shaft (2). The shaft extends proximally of the grip (103) in the form of a tail portion (150), which terminates in a fitting (151) configured to connect the first passageway (3) to a cryofluid source (not shown). The elongate shaft (2) encloses a first passageway (3) that is co-extensive with an inlet tube (17). A second passageway (4) is co-extensive with an outlet tube (18). The second passageway (4) may be open to the atmosphere proximally. The distal most end (26) of the inlet tube (17) typically projects into an expansion chamber (6) and may terminate in a Joule-Thomson orifice (7) which is formed at the distal most end (32) of the first passageway (3).

The inlet tube (17) is configured to deliver a cryogas under pressure from a cryofluid source (not shown in this figure). The cryogas expands on exiting the Joule-Thomson orifice (7) and evacuates via the outlet tube (18) to atmosphere at the distal opening (not shown in this figure).

A vacuum chamber (8) is formed over the outlet tube (18) bounded externally by an outer circumferential vacuum chamber wall (27). The vacuum chamber is configured to thermally insulate the shaft proximal to the operating head (5) and so prevent tissue damage proximal to the intended ice ball.

The shaft (2) extend through the grip portion (103) and may be continuous with the tail portion (150) as shown, or may form a union with a demountable tail portion (not shown) which provides the connection to the cryofluid source and optionally the proximal gas evacuation port(s).

The grip portion (103) has a diameter greater than the vacuum chamber wall (27) and provides a stiffened region of the shaft which prevents flexing of the shaft and protects the shaft during manipulation. In one arrangement, the grip portion (103) comprises a first sleeve (130) having an internal diameter greater than the vacuum chamber wall (27). The sleeve (130) fits over the vacuum chamber wall and provides additional stiffness to the shaft. A cylindrical cover (155) may be provided over the first sleeve and extending proximally past the proximal end (156) of the first sleeve (155) to cover at least a portion of the tail (150). Preferably, the cover (155) extends to the proximal end of the tail (not shown here).

The first sleeve (130) and the cover (155) may be held in place distally by a grip nose piece (157), typically of polymer material, such as polypropylene or PEEK, extending circumferentially about the vacuum sleeve wall (27) at the distal end (158) of the grip and configured to receive the distal most end (162) of a second sleeve (161) in a position axially outward of the first sleeve (130). This allows for wider sleeve and therefore a wider grip for easier manipulation. The grip nose piece extends circumferentially about the shaft (2), and may also extend circumferentially about the distal end (159) of the first sleeve (130) and the distal end (160) of the cover (155).

The proximal end (166) of the second sleeve (161) may be received in a similar manner by a grip tail piece (163) extending circumferentially about the vacuum sleeve wall (27) at the proximal end (164) of the grip.

The grip portion (103) may comprise a space (106) axially inwards of the second sleeve (161), which may optionally be filled with insulating material, but is preferably empty to provide a lighter grip.

An outer coating (not shown in this figure) may extend over the sleeve and optionally at least a portion of the nose piece and tail piece to provide a smooth surface to the grip. Again, a heat shrink tubing is useful in this regard.

What is claimed is:

1. A cryoprobe, comprising:
   an elongate shaft having a distal end and a proximate end; and
   an operating head at the distal end of the elongate shaft, wherein the operating head comprises an expansion chamber, the operating head being configured to ablate tissue that comes into contact with the operating head the expansion chamber being configured to accommodate high pressure expansion of a high pressure gas in excess of 1,000 psi;
   the elongate shaft comprising:
      a first passageway configured to provide the high pressure gas to the expansion chamber for the high pressure expansion and wherein the first passageway terminates in a Joule-Thomson orifice at its distal end;
      a second passageway for evacuating gas from the expansion chamber, wherein the second passageway is coaxially arranged around the first passageway; and
      a vacuum chamber coaxially arranged around the first passageway and the second passageway, the vacuum chamber is coextensive with a majority of a length of the second passageway;
   the cryoprobe additionally comprising an elongate stiffening element located towards the distal end of the elongate shaft configured to reduce flexing of the elongate shaft;
   wherein the elongate stiffening element comprises a grip portion having an inner diameter that is greater than a vacuum chamber wall and having proximal and distal tapered regions that provide a step down in the inner diameter to the vacuum chamber wall to hold the grip portion in place relative to the vacuum chamber at the proximal and distal ends of the grip portion, the grip portion being arranged about the elongate shaft such that the grip portion is circumferentially spaced apart from the vacuum chamber wall to thereby form an insulating space therebetween and arranged along the elongate shaft such that the grip portion is spaced apart from the operating head by a portion of the elongate shaft such that the grip portion is spaced apart from the tissue to be ablated when the operating head is ablating the tissue; and
   wherein the grip portion is provided by a first sleeve and further comprising a coating provided over the first sleeve to thereby seal the first sleeve to the vacuum chamber wall, the cryoprobe further comprising a covering extending at least from the grip portion to a proximal portion of a tail portion of the shaft to thereby provide protection to the tail portion and reduce kinking within the tail portion, and wherein the coating is provided by a second sleeve that covers at least a distal portion of the covering.

2. The cryoprobe according to claim 1 wherein a cross section of the elongate shaft is from 0.9 to 2.0 mm in diameter.

3. The cryoprobe according to claim 1 wherein the elongate shaft and operating head combined extend distally beyond the elongate stiffening element up to 100 mm such that the cryoprobe is about 150 millimeters in length or greater.

4. The cryoprobe according to claim 1 wherein the elongate stiffening element is arranged coaxially about the elongate shaft.

5. The cryoprobe according to claim 1 further comprising a single heat exchange arrangement consisting of an exchange of heat energy between the first passageway and the second passageway, the first and second passageways being arranged linearly and concentrically within the elongate shaft.

6. The cryoprobe according to claim 1 wherein a cross section of the elongate shaft is about 1.2 mm in diameter.

7. The cryoprobe according to claim 1 further comprising a tail portion extending from the grip portion such that the grip portion is continuous with the elongate shaft.

8. The cryoprobe according to claim 1 wherein the elongate shaft encloses the first passageway, the first passageway being co-extensive with an inlet tube, the second passageway being co-extensive with an outlet tube that projects into the operating head, the vacuum chamber being bounded externally by an outer circumferential vacuum chamber wall and internally by a wall of the outlet tube such that the vacuum chamber is formed as an extension of the elongate shaft and has the same diameter of the elongate shaft.

9. The cryoprobe according to claim 1 wherein the second passageway is formed by a second passageway wall coaxially arranged around the first passageway, and wherein the vacuum chamber is bounded externally by the vacuum chamber wall and internally by the second passageway wall, wherein at least one of:
a proximal end of the vacuum chamber wall terminates along the second passageway wall, and
a distal end of the vacuum chamber wall terminates along the second passageway wall.

10. The cryoprobe according to claim 1, wherein the expansion chamber is configured to accommodate the high pressure expansion of the high pressure gas at up to 4,500 psi.

11. A cryosurgical system comprising a cryoprobe and a source of cryofluid and a control configured to control a delivery of cryofluid to the cryoprobe:
the cryoprobe comprising:
an elongate shaft having a distal end and a proximate end; and
an operating head at the distal end of the elongate shaft, wherein the operating head comprises an expansion chamber, the operating head being configured to ablate tissue that comes into contact with the operating head the expansion chamber being configured to accommodate high pressure expansion of a high pressure gas such that the cryoprobe produces ice balls in excess of 10 millimeters in diameter within minutes;
the elongate shaft comprising:
a first passageway configured to provide the high pressure gas to the expansion chamber and wherein the first passageway terminates in a Joule-Thomson orifice at its distal end;
a second passageway for evacuating gas from the expansion chamber, wherein the second passageway is coaxially arranged around the first passageway; and
a vacuum chamber coaxially arranged around the first passageway and the second passageway, the vacuum chamber is coextensive with a majority of a length of the second passageway;
the cryoprobe additionally comprising an elongate stiffening element located towards the distal end of the elongate shaft configured to reduce flexing of the elongate shaft;
wherein the elongate stiffening element comprises a grip portion having an inner diameter that is greater than a vacuum chamber wall and proximal and distal tapered regions that provide a step down in the inner diameter to the vacuum chamber wall to hold the grip portion in place relative to the vacuum chamber at the proximal and distal ends of the grip portion, the grip portion being arranged about the elongate shaft such that the grip portion is circumferentially spaced apart from the vacuum chamber wall to thereby form an insulating space therebetween and arranged along the elongate shaft such that the grip portion is spaced apart from the operating head by a portion of the elongate shaft such that the grip portion is spaced apart the tissue to be ablated when the operating head is ablating the tissue; and
wherein the grip portion is provided by a first sleeve and further comprising a coating provided over the first sleeve to thereby seal the first sleeve to the vacuum chamber wall, the cryoprobe further comprising a covering extending at least from the grip portion to a proximal portion of a tail portion of the shaft to thereby provide protection to the tail portion and reduce kinking within the tail portion, and wherein the coating is provided by a second sleeve that covers at least a distal portion of the covering.

12. The cryosurgical system according to claim 11 wherein a cross section of the elongate shaft is from 0.9 to 2.0 mm in diameter.

13. The cryosurgical system according to claim 12 wherein a cross section of the elongate shaft of the cryoprobe is about 1.2 mm in diameter.

14. The cryosurgical system according to claim 11 wherein the elongate stiffening element is arranged coaxially about the elongate shaft.

15. The cryosurgical system according to claim 11 further comprising a single heat exchange arrangement consisting of an exchange of heat energy between the first passageway and the second passageway, the first and second passageways being arranged linearly and concentrically within the elongate shaft.

16. The cryosurgical system according to claim 11 wherein the cryoprobe further comprises a tail portion extending from the grip portion such that the grip portion is continuous with the elongate shaft.

17. The cryosurgical system according to claim 11 wherein the cryoprobe is arranged to have the elongate shaft enclose the first passageway, the first passageway being co-extensive with an inlet tube, the second passageway being co-extensive with an outlet tube that projects into the operating head, the vacuum chamber being bounded externally by an outer circumferential vacuum chamber wall and internally by a wall of the outlet tube such that the vacuum chamber is formed as an extension of the elongate shaft and has the same diameter of the elongate shaft.

18. A method of ablating a patient tissue, the method comprising:
placing a tip of a cryoprobe within or adjacent to a tissue to be ablated, the cryoprobe comprising:
an elongate shaft having a distal end and a proximate end, a cross section of the elongate shaft of the cryoprobe being about 1.2 mm in diameter;

an operating head at the distal end of the elongate shaft, wherein the operating head comprises an expansion chamber, the operating head being configured to ablate tissue that comes into contact with the operating head;

the elongate shaft comprising:
- a first passageway configured to provide high pressure gas to the expansion chamber and wherein the first passageway terminates in a Joule-Thomson orifice at its distal end;
- a second passageway for evacuating gas from the expansion chamber, wherein the second passageway is coaxially arranged around the first passageway; and
- a vacuum chamber coaxially arranged around the first passageway and the second passageway, the vacuum chamber is uniformly coextensive with a majority of a length of the second passageway;

the cryoprobe additionally comprising an elongate stiffening element located towards the distal end of the elongate shaft configured to reduce flexing of the elongate shaft; delivering a cryogas to the Joule-Thomson orifice, via the first passageway, at a pressure sufficient to cause cooling of a probe tip of the cryoprobe to a cryogenic temperature to freeze the tissue that is in contact with the probe tip, wherein the elongate stiffening element comprises a grip portion having an inner diameter that is greater than a vacuum chamber wall and proximal and distal tapered regions that provide a step down in the inner diameter to the vacuum chamber wall to hold the grip portion in place relative to the vacuum chamber at the proximal and distal ends of the grip portion, the grip portion being arranged about the elongate shaft such that the grip portion is circumferentially spaced apart from the vacuum chamber wall to thereby form an insulating space therebetween and arranged along the elongate shaft such that the grip portion is spaced apart from the operating head by a portion of the elongate shaft such that the grip portion is spaced apart the tissue to be ablated when the operating head is ablating the tissue, wherein the grip portion is provided by a first sleeve and further comprising a coating provided over the first sleeve to thereby seal the first sleeve to the vacuum chamber wall, the cryoprobe further comprising a covering extending at least from the grip portion to a proximal portion of a tail portion of the shaft to thereby provide protection to the tail portion and reduce kinking within the tail portion, and wherein the coating is provided by a second sleeve that covers at least a distal portion of the covering; and subsequently thawing the tissue.

19. The method according to claim 18 wherein the tissue is thawed by delivering a warming gas to the Joule-Thomson orifice at a pressure sufficient to cause warning of the probe tip thereby thawing the tissue.

\* \* \* \* \*